United States Patent [19]

Ledermann

[11] Patent Number: 4,938,694
[45] Date of Patent: Jul. 3, 1990

[54] SCREW IMPLANT

[75] Inventor: Philippe Ledermann, Herzogenbuchsee, Switzerland

[73] Assignee: Friedrichsfeld GmbH, Keramik-und Kunststoffwerke, Mannheim, Fed. Rep. of Germany

[21] Appl. No.: 230,828

[22] Filed: Aug. 11, 1988

[30] Foreign Application Priority Data

Aug. 11, 1987 [DE] Fed. Rep. of Germany ....... 3726616

[51] Int. Cl.⁵ ................................................ A61C 8/00
[52] U.S. Cl. ..................................... 433/173; 433/174
[58] Field of Search ............... 433/174, 173, 175, 176, 433/172

[56] References Cited

U.S. PATENT DOCUMENTS

| 4,362,511 | 12/1982 | Bolt ...................................... 433/220 |
| 4,722,688 | 2/1988 | Lonca .................................. 433/173 |
| 4,758,160 | 7/1988 | Ismail ................................... 433/174 |
| 4,790,753 | 12/1988 | Fradera ................................ 433/174 |

FOREIGN PATENT DOCUMENTS 1961531 7/1970 Fed. Rep. of Germany .
2413883 9/1975 Fed. Rep. of Germany .
724912 2/1955 United Kingdom ................. 433/172

OTHER PUBLICATIONS

Ledermann, Die Quintessenz, die Monatszeitschrift fuer den praktizierenden Zahnarzt, (The Quintessence, the Monthly Magazine for the Practicing Dentist), Nov. 1984, Report No. 6678, pp. 1-11.

Primary Examiner—Cary E. Stone
Attorney, Agent, or Firm—Foley & Lardner, Schwartz, Jeffery, Schwaab, Mack, Blumenthal & Evans

[57] ABSTRACT

A screw implant for securing a dental prosthesis comprising a threaded part (4) which can be screwed into the jaw, and an occlusal structural support (2) which has a conical head (8) and an inside thread (22) for an occlusal screw (24). A cap (12) is attached by means of the occlusal screw to the head. The screw head (26) is supported by a bearing surface (28) on the occlusal end face (30) of the cap, and the outer diameter of the screw head adjacent the bearing surface is substantially the same size as the outer diameter of the end face of the cap. The screw implant is simple to produce and manipulate and improves oral hygiene.

14 Claims, 1 Drawing Sheet

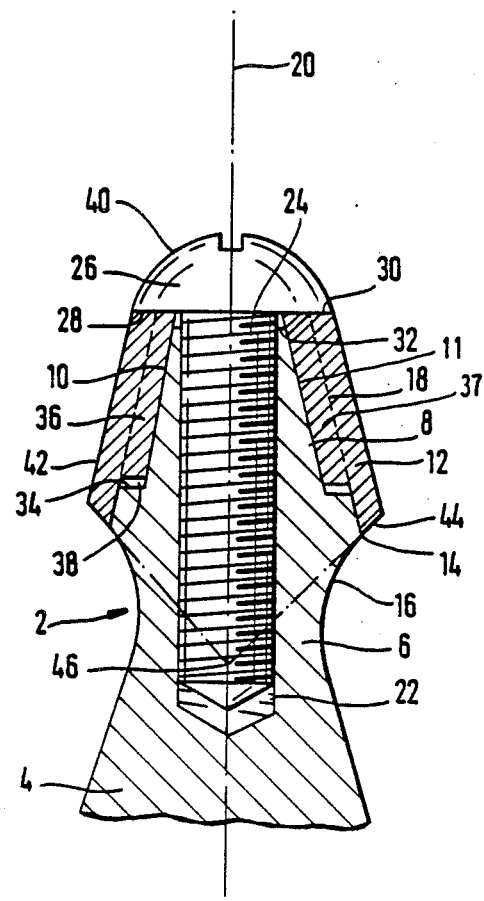

SCREW IMPLANT

BACKGROUND OF THE INVENTION

The present invention relates to a screw implant for securing a dental prosthesis, comprising a threaded part which can be screwed into a jaw, and an occlusal structural support having a conical head and an inside thread for an occlusal screw, by means of which a cap can be secured on the conical outer face of the head.

DE-OS 1,961,531 discloses such a screw implant whose structural support has a conical head on which a disk-shaped cap is screwed by means of a flatheaded screw. The flat surface of the screw head lies in the same plane as the likewise flat occlusal end face of the cap, in which connection, as a result of production tolerances, an annular gap between the screw head and the cap can scarcely be avoided in practice. The cap comprises a conical bore for receiving the screw head, and a corresponding conical surface is also provided for the screw head in the upper end of the threaded bore in the structural support. The outer face of the head of the structural support and, correspondingly, the inner face of the cap bearing thereon are conical, opening downwards to the thread of the structural support. The various conical surfaces, and also the end face of the structural support on which the cap bears with its edge, require an extremely high finishing accuracy. Problems arise above all with the oppositely disposed conical surfaces of the screw on the one hand, and of the outer face of the head of the occlusal structural support on the other hand. There is a considerable risk of gaps being formed between the head, cap and screw head. Such gaps represent a significant risk of development of infectious decay centers and are altogether disadvantageous with respect to the existing hygienic requirements.

DE-OS 2,413,883 discloses an endosteal implant for securing a firmly fitting dental prosthesis, which implant has a support comprising two sections. The one section is implanted into the jaw and comprises a blind bore extending substantially over the entire length and having an inside thread. The other section, which serves to secure a dental prosthesis, has a pin with an outside thread which can be screwed into the inside thread of the first section. Arranged between these sections is a flat, cylindrical ring of an elastic material, the thickness of this ring corresponding approximately to the thickness of the mucosa covering. Following the implantation of the lower section, instead of the second section, an auxiliary section is first screwed into the lower section, in which connection, by means of the elastic ring, it is intended to achieve a tight seal between the head of the auxiliary section and the lower section of the support. This auxiliary section is designed as a screw and remains in the lower section until the lower section has become completely incorporated into the jaw-bone. Thereafter the auxiliary section is removed and the second section of the support is screwed in its place into the lower section, so that, finally, the dental prosthesis can then be screwed to the second section.

Furthermore, a screw implant is described in the German periodical *Die Quintessenz, die Monatszeitschrift fur den praktizierenden Zahnarzt* (The Quintessence, the Monthly Magazine for the Practicing Dentist), November 1984, Report No. 6678, pages 1-11. This screw implant, which has proven satisfactory in practice for over 10 years, comprises a self-tapping threaded part which provides a large contact area over a short bone length and ensures optimum primary stability. By virtue of the titanium plasma coating of the threaded part, an enlarged contact area is obtained, this providing advantages with respect to the biocompatibility. The screw implant can be inserted transgingivally as a single implant, or several screw implants can be interlocked by means of a bar in order to construct a bar prosthesis. In this case, a cap is placed on the conical head and is secured by means of a screw engaged in the inside thread. The head has four continuous longitudinal grooves in its conical outer face which are used for the application of a tool when screwing into the jaw. Continuous grooves of this type have proven disadvantageous with respect to the hygienic requirements. The recessed-head screw to be screwed into the inside thread of the screw implant has a flat head which is countersunk below the top edge or end face of the cap. The end face of the cap is situated on an annular attachment inside which the screw head is arranged, which leads to deposits of filth and from which disadvantages arise with respect to hygienic suitability.

SUMMARY OF THE INVENTION

It is the object of the present invention to provide an improved screw implant for securing a dental prothesis.

Another object of the invention is to improve the aforementioned type of screw implant in such a way that good hygiene is facilitated.

It is also an object of the present invention to provide a screw implant which can be produced simply and can be readily installed and manipulated.

These and other objects of the invention are achieved by providing a screw implant for securing a dental prosthesis, comprising a threaded part which can be screwed into a jaw, and an occlusal structural support which has a head with a conical outer face and an inside thread for receiving an occlusal screw having a screw head, by means of which screw a cap or an open topped annular truncated casing can be secured to the conical outer face of the head, wherein the screw head bears via a bearing surface against the occlusal end face of the cap; the outer diameter of the screw head adjacent the bearing surface is substantially the same size as the outer diameter of the occlusal end face of the cap; the top of the head of the structural support is spaced a distance from the bearing surface of the screw, and the cervical end face of the cap is designed as a continuous extension of a neck face of the structural support.

The proposed screw implant is distinguished by a particularly hygienically compatible construction. By virtue of the aforementioned design of the screw head and its bearing on the occlusal end face of the cap, areas are avoided in which bacteria or the like could settle. The screw head is convex or lens-like in form and ensures accurate attachment of the cap in a manner compatible with hygienic requirements. According to the invention the cap and, similarly, the conical head of the structural support are each rotationally symmetrical in form. The cap advantageously is made of gold or of a corresponding dental gold alloy. The bearing surface of the screw head lies flat against the end face of the cap and, because of the identical outer diameters of the faces, a gap-free transition is assured between the cap and the outer face of the screw head. According to the invention the cap is designed as a conical sleeve of constant wall thickness. The outer face of the screw head is moreover rounded and merges directly into the conical outer face of the cap. The head of the structural support has a continuous, smooth, conical outer face, and the cap is compressed by means of the screw with its conical inner face against the conical head of the structural support.

If desired, at least one, advantageously two, longitudinal grooves can be provided. The longitudinal grooves which start at the top of the conical head do not extend over the entire length of the head, but end before the cervical end face of the cap. Thus, in this area too, a bacteria-proof seal is assured between the cap and the head, by which means a decisive improvement in hygiene is achieved in a reliable manner. In contrast to the hitherto conventional four longitudinal grooves distributed symmetrically around the circumference of the head, only two shortened longitudinal grooves are provided, so that also in this respect, the risk of developing centers of infectious decay is considerably reduced.

In addition, the cervical end face provided at the opposite end of the cap from the occlusal end face, does not lie in a parallel plane to the occlusal end face, but instead represents a continuous extension of the rounded face of the neck portion of the structural support which is designed in the form of a constriction. The hour-glass shaped, constricted neck face is highly polished. These measures have proven especially advantageous with regard to accurate fitting and adaption of the crown. As a result of this design, after incorporation of the screw implant, optimum conditions exist for the firm attachment of the mucous membrane, since the previously existing sharp edges in this area are now avoided by means of the polished surface.

BRIEF DESCRIPTION OF THE DRAWING

The invention will be described hereinafter in further detail with reference to an illustrative preferred embodiment shown in the accompanying drawing, which is a longitudinal sectional view through the screw implant according to the invention.

DETAILED DESCRIPTION OF PREFERRED EMBODIMENTS

The accompanying drawing figure shows a longitudinal section through a screw implant which has, in the occlusal area, a structural support 2 and also an endosteal threaded part 4 which is to be screwed in the jaw-bone and is shown here only in shortened form. The structural support 2 comprises a neck portion 6 and a conical head portion 8. According to the invention the head 8 and a cap 12 or an open topped annular truncated casing are designed with rotationally symmetrical configurations having smooth, conical outer and inner faces matched to each other.

Optionally, the head can have at least one longitudinal groove 10 in its outer face. Preferably, two diametrically opposite longitudinal grooves 10, 11 are provided in head outer face 18. The longitudinal grooves 10, 11 according to the invention do not extend over the entire length of the head 8, but end before the end edge 14 or neck 6 which, in the manner of an hour-glass constriction, has a curved face 16 which ends at the end edge 14 of the conical outer face 18 of the head 8. According to the invention the face 16 is highly polished, by which means optimum conditions are achieved for eventual firm attachment of the mucous membrane.

The structural support 2 comprises an inside thread 22 extending from the occlusal end in the direction of the longitudinal axis 20, into which inside thread a screw 24 can be screwed. It should be stressed that, after the threaded part 4, which desirably is provided with a self-tapping thread, has been screwed into the jaw-bone, the cap 12 is placed onto the conical head 8 and secured by means of the screw 24. Bars can be soldered in a known manner onto the outer face 42 of the cap 12, which is comprised of gold or generally of a castable dental alloy. The head 26 of the screw 24 has a bearing surface 28 which bears firmly against the occlusal end face 30 of the cap 12 such that there is no opening for the entry of bacteria. An essential point in this respect is that the top 32 of the structural support 2 is spaced a distance from the bearing surface 28, so that the conical inner face of the cap bears tightly against the outer face 18, which is advantageously highly polished, whereby the bearing surface 28 is pressed against the end face 30. For the aforementioned reasons a gap 38 is also provided in accordance with the invention between the inner end 34 of the longitudinal grooves 10, 11 and that parts 36, 37 of the cap 12 which are engaged in the longitudinal groove. The longitudinal groove 10 and also the cap parts 36, 37 extend only over a predetermined small angular range in the circumferential direction relative to the longitudinal axis 20.

The screw head 26 has a rounded outer face 40 which, in the area of the bearing surface 28, merges continuously into the outer circumferential surface 42 of the cap 12. The bearing surface 28 has the same outer diameter as the occlusal end face 30 of the cap 12, so that grooves or gaps, which are hygienically disadvantageous, are reliably avoided in this transition area. The other end face 44 of the cap 12 facing towards the threaded part 4 does not lie parallel to the occlusal end face 30, but is inclined like a cone in such a manner that the cone point 46 faces towards the threaded part 4. Instead of a conical design, the other end face 44 can also be of rounded design. An essential feature in this respect is that end face 44 represents a continuous extension of the outer face 16 of the neck 6, in order to avoid edges, grooves or the like, both in the transition to the neck face 16 and to the circumferential surface 42. This design has proven particularly advantageous for the mucous membrane attachment.

The foregoing description and examples have been set forth merely to illustrate the invention and are not intended to be exclusive. Since modifications of the described embodiments incorporating the spirit and substance of the invention may occur to persons skilled in the art, the scope of the invention should be limited solely with reference to the appended claims and equivalents.

What is claimed is:

1. A screw implant for securing a dental prosthesis, comprising a threaded part which can be screwed into a jaw, and an occlusal structural support which has a head with a top, a conical outer face, a cervical end edge and an inside thread; a single open-topped annular truncated casing having an annular occlusal end face and a cervical end face; an occlusal screw having a screw head with a bearing surface for securing the casing to the conical outer face of the head, said screw head having a diameter which is grater than the diameter of the top of said support head, wherein the screw is inserted in the thread of said head and the screw head bears via said bearing surface against the annular occlusal end face of the casing; the outer diameter of the screw head adjacent the bearing surface is substantially the same size as the outer diameter of the occlusal end face of the casing; the top of the head of the structural support is spaced a distance from the bearing surface of the screw, and the cervical end face of the casing is designed as a continuous extension of a neck face of the structural support.

2. A screw implant according to claim 1, wherein said screw head has a rounded configuration which merges smoothly into the outer circumferential surface of said casing to form a substantially continuous surface.

3. A screw implant according to claim 1, wherein the cervical end face of said casing has a substantially conical configuration which converges toward said threaded part of said implant.

4. A screw implant according to claim 1, wherein said bearing surface of said screw head is a flat surface located in a radial plane and extending in a radially outward direction to the circumferential surface of said casing.

5. A screw implant according to claim 1, wherein the occlusal end face of said casing is arranged in a radial plane and is formed as a flat annular surface extending radially outwardly to the circumferential surface of said casing.

6. A screw implant according to claim 1, wherein the outer face of said neck face is highly polished to eliminate rough edges.

7. A screw implant according to claim 6, wherein said outer face of said support head is highly polished to eliminate rough edges.

8. A screw implant according to claim 1, wherein said casing has an conical inner surface which matingly engages the conical outer surface of said head, and said cervical end face merges directly and continuously into said neck face.

9. A screw implant according to claim 1, wherein said open-topped annular casing is formed by an annular wall which has a uniform thickness along its axial length.

10. A screw implant according to claim 9, wherein said occlused end face defines an annular surface has a radial width equal to the radial thickness of said annular casing.

11. A screw implant according to claim 1, wherein said screw head bears via an annular margin of said bearing surface against the occlusal end face of the casing, and a substantially annular space is formed between the top of the support head and bearing surface of the screw.

12. A screw implant for securing a dental prosthesis, comprising a threaded part which can be screwed into a jaw; an occlusal structural support which has a head with a conical outer face, a cervical end edge and an inside thread; a cap adapted to be received on said conical outer face of said head and having an occlusal end face and a cervical end face; an occlusal screw having a screw head with a bearing surface for securing said cap to the conical outer face of the head, wherein the screw is inserted in the inside thread and the screw head bears via the bearing surface against the occlusal end face of the cap; the outer diameter of the screw head adjacent the bearing surface is substantially the same size as the outer diameter of the occlusal end face of the cap; the top of the head of the structural support is spaced a distance from the bearing surface of the screw; the cervical end face of the cap is designed as a continuous extension of a neck face of the structural support; and at least one longitudinal groove starts at the top of the structural support head, extends across only a part of the conical outer face of the structural support head, and ends at a distance before the cervical end edge of the structural support head, and said cap is provided with a cap part which engages in said longitudinal groove.

13. A screw implant according to claim 12, wherein said structural support head is formed with two diametrically opposite longitudinal grooves.

14. A screw implant according to claim 12, wherein a gap is provided between the lower end of said cap part which engages in said longitudinal groove and the lower end of said longitudinal groove.

* * * * *